(12) United States Patent
Lakshmi et al.

(10) Patent No.: US 7,399,609 B2
(45) Date of Patent: Jul. 15, 2008

(54) STAPHYLOCOCCUS DETECTION

(75) Inventors: Brinda B. Lakshmi, Woodbury, MN (US); Angela K. Dillow, Minneapolis, MN (US); M. Benton Free, St. Paul, MN (US); John S. Huizinga, Dellwood, MN (US); Patrick A. Mach, Shorewood, MN (US); Dasaratha V. Sridhar, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 684 days.

(21) Appl. No.: 10/960,491

(22) Filed: Oct. 7, 2004

(65) Prior Publication Data

US 2006/0019330 A1  Jan. 26, 2006

Related U.S. Application Data

(60) Provisional application No. 60/533,171, filed on Dec. 30, 2003.

(51) Int. Cl.
C12Q 1/14 (2006.01)
G01N 33/569 (2006.01)
G01N 9/00 (2006.01)
G01N 11/00 (2006.01)
C12N 1/24 (2006.01)
C12N 13/00 (2006.01)

(52) U.S. Cl. .......................... 435/36; 435/7.33; 435/30; 435/173.9; 73/32 A; 73/53.01

(58) Field of Classification Search .................... None
See application file for complete search history.

(56) References Cited

U.S. PATENT DOCUMENTS

| | | | |
|---|---|---|---|
| 4,756,884 A | 7/1988 | Hillman et al. | |
| 4,902,616 A | 2/1990 | Fournier et al. | |
| 4,963,498 A | 10/1990 | Hillman et al. | |
| 5,076,094 A | 12/1991 | Frye et al. | |
| 5,117,146 A | 5/1992 | Martin et al. | |
| 5,151,110 A | 9/1992 | Bein et al. | |
| 5,235,235 A | 8/1993 | Martin et al. | |
| 5,763,283 A | 6/1998 | Cernosek et al. | |
| 5,814,525 A | 9/1998 | Renschler et al. | |
| 5,836,203 A | 11/1998 | Martin et al. | |
| 5,892,144 A | 4/1999 | Meller et al. | |
| 6,232,139 B1 | 5/2001 | Casalnuovo et al. | |
| 6,271,040 B1 | 8/2001 | Buechler | |
| 6,686,169 B2 | 2/2004 | Fournier et al. | |

FOREIGN PATENT DOCUMENTS

| | | |
|---|---|---|
| DE | 40 35 751 A1 | 8/1991 |
| EP | 0 532 430 A1 | 7/1992 |
| EP | 0212314 | 4/1994 |
| JP | 05 034349 | 2/1993 |
| JP | 11-28099 | 2/1999 |
| WO | WO 02/079486 | 10/2002 |
| WO | WO 2002/082086 A2 | 10/2002 |
| WO | WO 03/025208 | 3/2003 |
| WO | WO 2005/064349 A2 | 7/2005 |
| WO | WO 2005/066092 A2 | 7/2005 |
| WO | WO 2005/075973 A2 | 8/2005 |

OTHER PUBLICATIONS

Saha et al. (2003) Probing the Viscoelasticity and Mass of a Surface-Bound Protein Layer with an Acoustic Wave Device. Langmuir 19: 1304-1311.*
Saha et al. (2003) Comparative Study of IgG Binding to Proteins G and A: Nonequilibrium Kinetic and Binding Constant Determination with the Acoustic Waveguide Device. Anal. Chem. 75:835-842.*
Gizeli et al. (2003) Sensitivity of the acoustic waveguide biosensor to protein binding as a function of the waveguide properties. Biosensors and Bioelectronics 18: 1399-1406.*
Cote et al. (2003) Emerging Biomendical Sensing Technologies and Their Applications. IEEE Sensors Journal 3(3): 251-266.*
Ivnitski et al. (1999) Review: Biosensors for detection of pathogenic bacteria. Biosensors and Bioelectronics 14: 599-624.*
Pavey et al. (2001) A rapid non-destructive method for the determination of *Staphylococcus epidermidis* adhesion to surfaces using quartz crystal resonant sensor technology. Lett. Appl. Microbiol. 33:344-348.*
Biosensors & Bioelectronics, Low-level detection of a *Bacillus anthracis* stimulant using Love-wave biosensors on 36° YX LiTaO$_3$, © 2003, pp. 1-11.
Infectious Diseases Research Center, Development of a Real-Time PCR Assay for Rapid Detection of Methicillin-Resistant *Staphylococcus aureus* Directly from Clinical specimens Containing a Mixture of Staphylococci, Huletsky et al., date unknown.
Infectious Diseases Research Center, Real-Time Detection of Clinically Relevant Bacterial Pathogens: Description and Preliminary Performances of a New System, Menard et al., date unknown.
Medical Laboratory Observer, Bacterial resistance: How to detect three types, Shima et al., Apr. 2004.
Science Direct.com, Biosensors and Bioelectronics: Low-level detection of a *Bacillus anthracis* stimulant using Love-wave biosensors on 36° YX LiTaO$_3$, vol. 19, Issue 8, Mar. 15, 2004, pp. 849-859.
Conversion of fibrinogen to fibrin induced by preferential release of fibrinopeptide B, Dyr et al., 1989.
Multiple Binding Sites in the Interaction between an Extracellular Fibrinogen-binding Protein from *Staphylococcus aureus* and Fibrinogen, The Journal of Biological Chemistry, 1998, vol. 273, No. 21, Issue of May 22, pp. 13177-13181.
American Society for Microbiology, Gram-Positive Pathogens, © 2000, Extracellular Enzymes, Staffan Arvidson.
American Society for Microbiology, Gram-Positive Pathogens, © 2000, Pathogenicity Factors and Their Regulation, Richard Novick.
Contributions to Microbiology and Immunology, vol. 1, Staphylococci and Staphylococcal Infections, pp. 364-375 (Karger, Basel 1973); Mechanism of action of a staphylocoagulase and clumping factor, Wegrzynowicz et al.
Fibrinogen and Fibrin, Doolittle, Department of Chemistry, University of California at San Diego, LaJolla, California, 1984 Annual Reviews Inc.
Manual of Clinical Microbiology, *Staphylococcus* and *Micrococcus*; Bacteriology, pp. 288-289.

(Continued)

*Primary Examiner*—Lisa J Hobbs
(74) *Attorney, Agent, or Firm*—Carolyn A. Fischer; Nancy M. Lambert

(57) ABSTRACT

The invention relates to methods of detecting *staphylococcus*.

34 Claims, 4 Drawing Sheets

OTHER PUBLICATIONS

Analytica Chimica Acta (1998), A rapid method for determination of *Staphylococcus aureus* based on milk coagulation by using a series of piezoelectric quartz crystal sensor, Bao et al.

Moses et al., Plasma Deposition and Etching of Diamond-Like Carbon Films, AIChE Journal, Mar. 1991, vol. 37, No. 3, pp. 367-376.

Gizeli et al; "Sensitivity of the acoustic waveguide biosensor to protein binding as a function of the waveguide properties"; Biosensors & Bioelectronics;, 2003, 18; pp. 1399-1406.

Höök et al., "Chapter 40, Staphylococcal Surface Proteins," in *Gram-Positive Pathogens*, Fischetti et al., Eds., ASM Press, Washington, D.C. 2000, Title page, Publication page, and pp. 386-391.

Ivnitski et al., "Review, Biosensors for detection of pathogenic bacteria," *Biosensors & Bioelectronics*, 1999, 14:599-624.

Lim et al., "Structural basis for the β-lactam resistance of PBP2a from methicillin-resistant *Staphylococcus aureus*," *Nat. Struct. Biol.*, Nov. 2002, 9(11):870-876.

Mazmanian et al., "An iron-regulated sortase anchors a class of surface protein during *Staphylococcus aureus* pathogenesis," *Proc. Natl. Acad. Sci.*, Feb. 2002, 99(4):2293-2298.

Navarre et al., "Surface Proteins of Gram-Positive Bacteria and Mechanisms of Their Targeting to the Cell Wall Envelope," *Microbiol Mol Biol Rev.* 1999, 63(1):174-229.

Navarre et al., "Surface Proteins of Gram-Positive Bacteria and Mechanisms of Their Targeting to the Cell Wall Envelope," *Microbiol Mol Biol Rev.* 1999, 63(1);174-229.

Navarre et al., "Anchor Structure of Staphylococcal Surface Proteins. II. COOH-terminal structure of muramidase and amidase-solubilized surface protein," *J. Biol. Chem.*, Oct. 1998, 273(44):29135-29142.

Projan, "Chapter 48, Antibiotic Resistance in the Staphylococci," in *Gram-Positive Pathogens*, Fischetti et al., Eds., ASM Press, Washington, D.C. 2000, Title page, Publication page, and pp. 463-469.

Stapleton et al., "Methicillin resistance in *Staphylococcus aureus*:mechanisms and modulation," *Sci Prog.* 2002 ,85 (Pt. 1):57-72.

Sugai et al., "Purification and Molecular Characterization of Glycylglycine Endopeptidase Produced by *Staphylococcus capitis* EPK.1," *J. Bacteriol.*, Feb. 1997, 179(4):1193-1202.

Warnes et al; Development of an enzyme-linked immunosorbent assay for staphylococcal protein A produced in *Escherichia coli* by pUC8 based plasmids containing the *Staphylococcus aureus* Cowan;I protein A gene; Journal of Immunological Methods; 93; 1986; pp. 63-70.

L. Bao et al.; "A Rapid Method of Determination of *Staphylococcus aureus* Based on Milk Coagulation by Using a Series Piezoelectric Quartz Crystal Sensor"; *Analytica Chimica Acta*: 369 (1998); Sep. 30, 1997; pp. 139-145.

O. Tamarin et al; "Real Tim Device for Biosensing: Design of a Bacteriophage Model Using Love Acoustic Waves"; *Biosensors Bioelectronics*; 18 (2003); May 15, 2002; pp. 755-763.

K.D. Pavey et al.; "A Rapid, Non-Destructive Method for Determination of *Staphylococcus epidermidis* Adhesion to Surface Using Quartz Crystal Resonant Sensor Technology"; Letters in Applied Microbiology 2001; *The Society for Applied Microbiology*; vol. 33, pp. 344-348.

M. Paulsson et al.; "Adhesion of Staphylococci to Chemically Modified and Native Polymers, and the Influence of Preadsorbed Fibronectin, Vitronectin and Fibrinogen"; *Biomaterials*; 1993, vol. 14, No. 11; pp. 845-853.

* cited by examiner

STAPHYLOCOCCUS DETECTION

CROSS REFERENCE TO RELATED APPLICATIONS

This application claims priority to U.S. Provisional Application Ser. No. 60/533,171 filed Dec. 30, 2003.

FIELD OF THE INVENTION

The invention relates to methods of detecting *staphylococcus*.

BACKGROUND OF THE INVENTION

*Staphylococcus aureus* ("*S. aureus*") is a pathogen causing a wide spectrum of infections including superficial lesions such as small skin abscesses and wound infections; systemic and life threatening conditions such as endocarditis, pneumonia and septicemia; as well as toxinoses such as food poisoning.

According to pp. 288-289 of the Manual of Clinical Microbiology (ASM Press, Washington D.C., 1995) the ability to clot plasma continues to be the most widely used and generally accepted criterion for the identification of pathogenic staphylococci associated with acute infection, i.e. *S. aureus* in humans and animals and *S. intermedius* and *S. hyicus* in animals. At least two different coagulase tests have been described: a tube test for free coagulase and slide test for bound coagulase or clumping factor. While the tube test is definitive, the slide test may be used as a rapid screening test technique to identify *S. aureus*. A variety of plasma types may be used for either test, however dehydrated rabbit plasma containing ethylenediaminetetraacetate is commercially available.

The tube coagulase test is described as being performed by mixing 0.1 ml of an overnight culture in brain heart infusion broth with 0.5 ml of reconstituted plasma, incubating the mixture at 37° C. in a water bath or heat block for 4 hours and observing the tube for clot formation by slowly tilting the tube for clot formation. Alternatively a large, well-isolated colony on nonhibitory agar can be transferred into 0.5 ml of reconstituted plasma and incubated as described above. Any degree of clotting constitutes a positive test. However, a flocculent or fibrous precipitate is not a true clot and should be recorded as a negative result. Incubation of the test overnight has been recommended for *S. aureus* since a small number of strains may require longer than 4 hours for clot formation. For those uncommon *S. aureus* strains requiring a longer clotting period, other characteristics should be tested to confirm identity.

The slide coagulase test is described as being performed by making a heavy uniform suspension of growth in distilled water, stirring the mixture to a homogeneous compositions so as not to confuse clumping with auto agglutination, adding a drop of plasma and observing for clumping within 10 seconds. The slide test is rapid and more economical of plasma than the tube test. However, 10 to 15% of *S. aureus* strains may yield a negative result, which requires that the isolate by reexamined by the test tube test. Slide tests must be read quickly because false-positive results may appear with reaction times longer than 10 seconds. Alternative methods for the slide test include commercial hemagglutination-slide tests for clumping factor and commercial latex agglutination tests that detect both clumping factor and protein A. Further, a latex agglutination test that detects clumping factor, protein A, and serotype 5 and 8 capsular polysaccharides of *S. aureus* is also available. When the organism being tested is suspected of being *S. aureus*, it is recommended that negative slide tests be confirmed by the tube coagulase test.

The Journal of Biological Chemistry (Vol. 273, No. 21, Issue of May 22, pp. 13177-13181, 1998 describes five different fibrinogen-binding proteins from *S. aureus*. Three of these fibrinogen-binding proteins were purified. One of such proteins is coagulase, a protein also able to bind to prothrombin. The third, designated as an extracellular fibrinogen-binding (Efb) protein was found to be incident in 100% of *S. aureus* isolates tested, although the level varied. It is further reported that the presence of $Ca^{2+}$ or $Zn^{2+}$ enhances the precipitation of the proteins from equimolar mixtures of Efb and fibrinogen.

Analytica Chimica Acta 369 (1998) 139-145 describes "a series piezoelectric quartz crystal (SPQC) biosensor was utilized to determine the number of bacteria based on the coagulation of milk in which *S. aureus* had grown. Compared with the method based on PQC with a thin film, earlier it had the advantage that no dilution of the medium was needed and cease of the oscillation can be avoided throughout the experiment. Moreover, it was rapid, the turning point time (TT) for quantitative detection which was the time at which the frequency begins to return after a drop is response curve was easy to determine and there was a good relation between TT and the logarithm of the initial concentration of *S. aureus* in the range of $2.4 \times 10^2 - 2.4 \times 10^5$ cell $ml^{-1}$."

Although methods of detecting *S. aureus* have been described in the art, there would be advantage in improved methods of detection.

SUMMARY OF THE INVENTION

Methods of detecting *Staphylococcus aureus* are described.

In one embodiment, the method comprises providing a test sample, providing a *Staphylococcus aureus* reactant, combining the test sample and the *Staphylococcus aureus* reactant resulting in a change of at least one physical property, and detecting the change with a shear horizontal surface acoustical wave biosensor.

In another embodiment, the method comprises providing a test sample, providing fibrinogen, combining the test sample and the fibrinogen wherein a test sample comprising *Staphylococcus aureus* results in a change of at least one physical property; and detecting the change with an acoustic mechanical biosensor.

For all of the embodiments described, the test sample may comprises a relatively low concentration of *Staphylococcus aureus* such as about $5 \times 10^4$ cfu/ml, about $5 \times 10^3$ cfu/ml, about 1000 cfu/ml, about 500 cfu/ml, and any concentration therebetween. Further, the detection time is relatively short such as about 150 minutes, about 100 minutes, about 60 minutes, about 30 minutes, and any detection times therebetween.

For all of the embodiments described, the change in at least one physical property is preferably a change in viscosity and/or a change in bound mass that results in a change in wave phase and or wave velocity. The test sample may comprise low volume ranging from about 0.5 ml to about 1.5 ml. The acoustic mechanical biosensor preferably comprises a waveguide such as polyimide and polystyrene.

For all of the embodiments described, the test sample and *Staphylococcus aureus* reactant may be combined in a variety of suitable manners. In one aspect, the *Staphylococcus aureus* reactant and test sample are provided to the acoustic mechanical biosensor as separate portions, yet in any order. In some embodiments, the step of combining the test sample and

*Staphylococcus aureus* reactant results in formation of a solid. The method may further comprise separating the solid.

Figure 1:
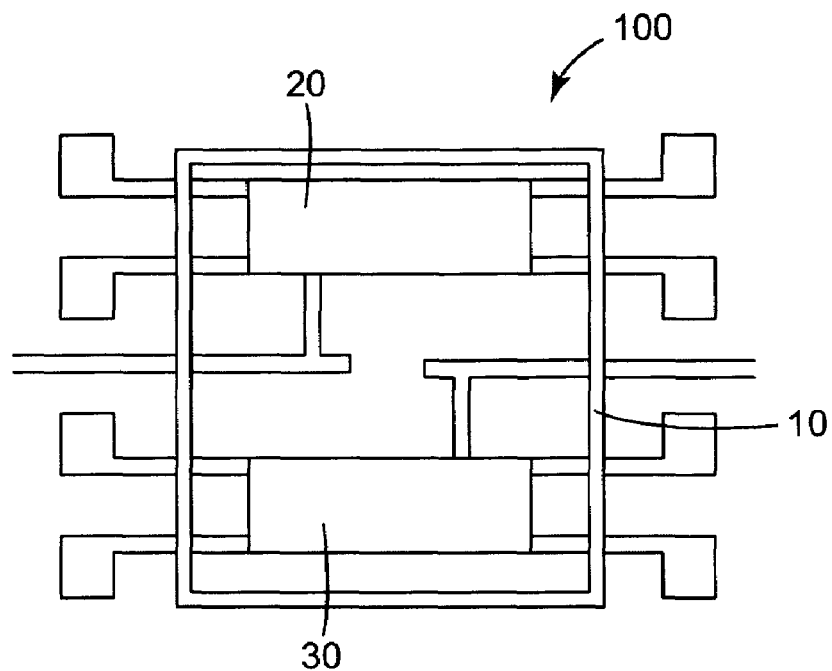
FIG. 1 depicts a plan view of the sensor surface between the interdigital transducers.

FIG. 2 depicts the sensogram from a acoustic mechanical biosensor after injection of water.

FIG. 3*a*-3*c* depict the sensograms from a acoustic mechanical biosensor comprising a polyimide waveguide after injection of *S. aureus* at concentrations of 500 cfu/ml, 5000 cfu/ml and 50,000 cfu/ml respectively.

FIG. 4*a*-4*c* depict the sensograms from a acoustic mechanical biosensor comprising a polystyrene waveguide after injection of *S. aureus* at concentrations of 500 cfu/ml, 5000 cfu/ml and 50,000 cfu/ml respectively.

FIG. 5 is a graph depicting phase shift as a function of *S. aureus* concentration.

FIG. 6 is a graph depicting change in propagation velocity as a function of *S. aureus* concentration utilizing the polyimide as the waveguide.

DETAILED DESCRIPTION OF THE PREFERRED EMBODIMENTS

Unlike the classical clinical assays, such as tube and slide coagulase tests, the present invention employs an acoustic mechanical biosensor that detects a change in at least one physical property and produces a signal in response to the detectable change. The signal in response to the change may be recorded on tangible output such as a piece of paper. For example, in the case of acoustic mechanical biosensors, the wave phase and/or velocity and/or frequency response of a shear horizontal surface acoustic wave may be recorded on a sensogram, thus providing a quantitative signal. For ease in operation, the acoustic mechanical biosensor preferably converts the quantitative output to a threshold signal. The acoustic mechanical biosensor device may include a screen display (e.g. liquid crystal display) that displays a "positive" or "negative" test result.

In the present invention, a biosensor that employs an acoustic mechanical means for detection is preferred. More preferably, the acoustic mechanical biosensor employed herein is a surface acoustic wave (SAW) biosensor. In these devices an acoustic wave is generated from an interdigital transducer (IDT) on a piezoelectric substrate either as a surface acoustic wave or as a bulk acoustic wave. A second IDT may convert the acoustic wave back to an electric signal for measurement. This is referred to as a delay line. Alternatively the device may operate as a resonator. The space between the two IDTs can be modified with coating that may include reactive molecules for chemical or biosensing applications.

With reference to FIG. 1, in some embodiments the acoustic mechanical biosensor surface 100 between the IDTs preferably comprises two delay lines. A first channel, i.e. the "active" channel 20 is provided for receipt of the test sample. The second channel, i.e. the "reference" channel 30 is provided as the baseline or control. Accordingly, the change in physical property is the difference between the active channel and the reference channel. The data may be transformed with mathematical algorithms in order to improve the sensitivity, as described U.S. Provisional Patent Application Ser. No. 60533177, filed Dec. 30, 2003, entitled "Estimating Propagation Velocity Through Surface Acoustic Wave Sensors", incorporated herein by reference.

Piezoelectric-based SAW biosensors typically operate on the basis of their ability to detect minute changes in mass or viscosity. As described in U.S. Pat. No. 5,814,525, the class of piezoelectric-based acoustic mechanical biosensors can be further subdivided into surface acoustic wave (SAW), acoustic plate mode (APM), or quartz crystal microbalance (QCM) devices depending on their mode of detection of mass changes.

In some embodiments, the acoustic mechanical biosensor comprises a reactant (e.g. antibody) that attaches the *S. aureus* biomolecule of interest to the surface of the piezoelectric acoustic mechanical biosensor. In other embodiments, the acoustic mechanical biosensor detects a physical change in a liquid (e.g. aqueous solution) such as a change in viscosity. The propagation velocity of the surface wave is a sensitive probe capable of detecting changes such as mass, elasticity, viscoelasticity, conductivity and dielectric constant. Thus, changes in any of these properties results in a detectable change in the surface acoustic wave. That is, when a substance comes in contacts with, absorbs, or is otherwise caused to adhere to the surface coating of a SAW device, a corresponding response is produced. APM can also be operated with the device in contact with a liquid. Similarly, an alternating voltage applied to the two opposite electrodes on a QCM (typically AT-cut quartz) device induces a thickness shear wave mode whose resonance frequency changes in proportion to mass changes in a coating material.

The direction of the acoustic wave propagation (e.g. in the plane parallel to the waveguide or perpendicular to the plane of the waveguide) is determined by the crystal-cut of the piezoelectric material from which the acoustic mechanical biosensor is constructed. SAW biosensors that have the majority of the acoustic wave propagating in and out of the plane (i.e. Rayleigh wave, most Lamb-waves) are typically not employed in liquid sensing applications since there is too much acoustic damping from the liquid contact with the surface.

For liquid sample mediums, a shear horizontal surface acoustic wave biosensor (SH-SAW) is preferably constructed from a piezoelectric material with a crystal-cut and orientation that allows the wave propagation to be rotated to a shear horizontal mode, i.e. in plane of the biosensor waveguide), resulting in reduced acoustic damping loss to the liquid in contact with the biosensor surface. Shear horizontal acoustic waves include thickness shear modes (TSM), acoustic plate modes (APM), surface skimming bulk waves (SSBW), Love-waves, leaky acoustic waves (LSAW), and Bleustein-Gulyaev (BG) waves.

In particular, Love wave sensors consist of a substrate supporting a SH wave mode such as SSBW of ST quartz or the leaky wave of 36°YXLi$TaO_3$. These modes are converted into a Love-wave mode by application of thin acoustic guiding layer or waveguide. These waves are frequency dependent and can be generated provided that the shear wave velocity of the waveguide layer is lower than that of the piezoelectric substrate. $SiO_2$ has been used as an acoustic waveguide layer on quartz. Other thermoplastic and crosslinked polymeric waveguide materials such as polymethylmethacrylate, phenol-formaldehyde resin (e.g. trade designation "Novalac"), polyimide and polystyrene, have also been employed.

Alternatively QCM devices can also be used with liquid sample mediums.

Biosensors employing acoustic mechanical means and components of such biosensors are known. See for example U.S. Pat. Nos. 5,076,094; 5,117,146; 5,235,235; 5,151,110; 5,763,283; 5,814,525; 5,836,203; 6,232,139; each incorporated herein by reference. SH-SAW devices can be obtained from various manufacturers such as Sandia National Laboratories, Albequerque, N. Mex. Certain SH-SAW biosensors are also described in "Low-level detection of a *Bacillus anthracis* stimulant using Love-wave biosensors of 36°YXLiTaO$_3$," accepted Aug. 22, 2003 by Biosensors and Bioelectronics. SAW biosensors, as well as methods of detecting biological agents, are also described in U.S. Provisional Patent Application Ser. No. 60/533,169, filed Dec. 30, 2003, entitled "Acousto-mechanical Detection Systems and Methods for Biological Agents", incorporated herein by reference.

In some embodiments, the acoustic mechanical biosensor includes only the waveguide layer and thus the biosensor is substantially free of *S. aureus* reactant (e.g. antibody). In this embodiment, the biosensor typically detects a change in viscosity. In other embodiments, the surface of the biosensor includes an *S. aureus* reactant (e.g. antibody). In this embodiment, the biosensor typically detects a change in viscosity and/or mass bound by the *S. aureus* reactant. For this embodiment, the biosensor preferably comprises an immobilization layer and tie layer(s).

An immobilization layer is provided for the purpose of binding the *S. aureus* reactant (e.g. antibody) to the surface. An exemplary immobilization layer includes N-acyl saccharin tricholoro silane. Suitable immobilization chemistry for use with the devices of the present invention include Applicants' Copending Applications U.S. patent application Ser. No. 10/713,174, filed Nov. 14, 2003; U.S. Provisional Application Ser. No. 60/533,162, filed Dec. 30, 2003; U.S. Provisional Application Ser. No. 60/533,169, filed Dec. 30, 2003; U.S. patent application Ser. No. 10/713,174, filed Nov. 14, 2003; U.S. Provisional Patent Application Ser. No. 60/533,178, filed Dec. 30, 2003 and U.S. patent application Ser. No. 10/896,392, filed Jul. 22, 2004. If the immobilization layer cannot be applied directly to the waveguide layer, a tie layer may be disposed between the waveguide and immobilization layer. An exemplary tie layer for use in combination with N-acyl saccharin tricholoro silane tie layers includes a layer of diamond-like glass, such as described in International Patent Application WO 01/66820 A1, incorporated herein by reference in its entirety. The diamond-like glass is an amorphous material that includes carbon, silicon, and one or more elements selected from hydrogen, oxygen, fluorine, sulfur, titanium, or copper. Some diamond-like glass materials are formed from a tetramethylene silane precursor using a plasma process. A hydrophobic material can be produced that is further treated in an oxygen plasma to control the silanol concentration on the surface.

Diamond-like glass can be in the form of a thin film or in the form of a coating on another layer or material in the substrate. In some applications, the diamond-like glass can be in the form of a thin film having at least 30 weight percent carbon, at least 25 weight percent silicon, and up to 45 weight percent oxygen. Such films can be flexible and transparent. In some multilayer substrates, the diamond like glass is deposited on a layer of diamond-like carbon. The diamond-like carbon can, in some embodiments, function as a second tie layer or primer layer between a polymeric layer and a layer of diamond-like glass in a multilayer substrate. Diamond-like carbon films can be prepared, for example, from acetylene in a plasma reactor. Other methods of preparing such films are described U.S. Pat. Nos. 5,888,594 and 5,948,166, incorporated herein by reference, as well as in the article M. David et al., AIChE Journal, 37 (3), 367-376 (March 1991).

The method of the invention comprises providing a test sample, providing a *S. aureus* reactant, combining the test sample and the *S. aureus* reactant wherein a test sample comprising *S. aureus* (i.e. the analyte) results in a change of at least one physical property, and detecting the physical change with a biosensor (i.e. acoustical mechanical sensor such as a SH-SAW sensor).

"*S. aureus* reactant" refers to a constituent that is capable of interacting with *S. aureus* present in the test sample. Accordingly, the *S. aureus* reactant is a type of "detectable binding reagent" i.e. an agent that specifically recognizes and interacts or binds with an analyte (of interest to measure), wherein the agent has a property permitting detection when bound. "Specifically interact" means that a binding agent physically interacts with the analyte one wishes to measure, to the substantial exclusion of other analytes also present in the sample. The binding of a detectable binding reagent useful according to the invention has stability permitting the measurement of the binding. A detectable binding reagent can possess an intrinsic property that permits direct detection, or it can be labeled with a detectable moiety. "Detectable moiety" refers to a moiety that can be attached to a binding reagent that confers detection of the binding reagent by a particular method or methods. Detectable moieties include, but are not limited to radiolabels (e.g., $^{32}P$, $^{35}S$, $^{125}I$, etc.), enzymes (e.g., alkaline phosphatase, peroxidase, etc.), fluorophores (e.g., fluorescein, amino coumarin acetic acid, tetramethylrhodamine isothiocyanate (TRITC), Texas Red, Cy3.0, Cy5.0, green fluorescent protein, etc.) and colloidal metal particles.

Suitable methods for coating the devices of the present invention include Applicant's Co-pending Application U.S. Ser. No. 10/607698 filed Jun. 27, 2003.

The interaction produces a change in at least one physical property (e.g. bound mass and/or viscosity in the case of SH-SAW biosensors) that is detectable by the biosensor. Preferred *S. aureus* reactants include *S. aureus* (e.g. specific) antibody, fibrinogen, combinations thereof, and the like.

The test sample and *S. aureus* reactant may be combined in a variety of suitable manners. In one aspect, the *S. aureus* reactant (e.g. fibrinogen-containing solution) is provided to the acoustic mechanical biosensor and the (e.g. liquid) test sample is provided to the biosensor as separate portions, yet in any order. In another aspect, the (e.g. liquid) test sample and *S. aureus* reactant (e.g. fibrinogen-containing solution) are combined as a mixture and the mixture is provided to the acoustic mechanical biosensor. In other embodiments, the *S. aureus* reactant is incorporated into the acoustic mechanical biosensor surface and thus integral with the biosensing device. For example the surface of the waveguide may be coated with a fibrinogen-containing solution and optionally dried. Alternatively, an *S. aureus* antibody may be present of the acoustic mechanical biosensor surface, such antibody fixated by means of an immobilization layer. Although the acoustic mechanical biosensor surface may be coated with a *S. aureus* reactant near the time or immediately before injection of the test sample, for speed in operation it is preferred that the *S. aureus* reactant is coated and/or is incorporated during manufacture of the biosensor or component thereof.

Advantageously, the method of the invention has improved sensitivity. The present inventors have detected *S. aureus* at low-levels. As further described in the forthcoming examples, *S. aureus* can be detected at concentrations of $5 \times 10^4$ colony forming units ("cfu") per milliliter, $5 \times 10^3$ cfu/ml, and $5 \times 10^2$ cfu/ml. The minimum detection level is surmised to be about 100 cfu/ml. Accordingly, one of ordinary skill in the art appreciates that the method of the present invention can be employed to detect *S. aureus* at any concentration between about 100 cfu/ml and about $5 \times 10^2$ cfu/ml (e.g. any specific concentration between the stated concentrations at increments of 10 cfu/ml). *S. aureus* can be detected at high levels as well, ranging up to as much as $5 \times 10^7$ cfu/ml.

Alternatively, or in addition thereto, the method of the invention also advantageously result in an improved detection rate. The acoustic mechanical biosensor device employed herein is capable of detecting *S. aureus* in a relatively short period of time. For example, *S. aureus* can be detected at any of the concentrations previously described in less than 300 minutes (e.g. 250 minutes, 200 minutes, 150 minutes, 100 minutes). As further described in the forthcoming examples, *S. aureus* can be detected about 30 minutes or less.

Any suitable test sample may be injected into the sample port of the acoustic mechanical biosensor. As used herein "test sample" refers to a sample that may contain *S. aureus*. Preferably the sample is a liqu sample may be derived from any source, such as a physiological fluid, e.g., blood, saliva, ocular lens fluid, synovial fluid, cerebral spinal fluid, pus, sweat, exudate, urine, mucous, sputum, feces, lactation milk, or the like. Further, the test sample may be derived from a body site e.g. wound, skin, nares, scalp, nails, etc.

The art describes various patient sampling techniques for the detection of *S. aureus*. Such sampling techniques are suitable for the method of the present invention as well. It is common to obtain a sample from wiping the nares of a patient. A particularly preferred sampling technique includes the subject's (e.g. patient's) anterior nares swabbed with a sterile rayon swab. One swab is used to sample each subject, i.e. one swab for both nostrils. The sampling is performed by inserting the rayon swab (commercially available from Puritan, East Grinstead, UK under the trade designation "Pure-Wraps" dry or pre-moistened with an appropriate solution into the anterior tip of the subject's nostril and rotating the swab for two complete revolutions along the nares' mucosal surface. The swab is then cultured directly or extracted with an appropriate solution typically including water optionally in combination with a buffer and at least one surfactant.

Besides physiological fluids, other test samples may include other liquids as well as solid(s) dissolved in a liquid medium. Samples of interest may include process streams, water, soil, plants or other vegetation, air, (e.g. contaminated) surfaces and the like.

The test sample (e.g. liquid) may be subjected to prior treatment, such as dilution of viscous fluids. The test sample (e.g. liquid) may be subjected to other methods of treatment prior to injection into the sample port such as concentration, by filtration, distillation, dialysis, or the like; dilution, filtration, inactivation of natural components, addition of reagents, chemical treatment; etc.

In some embodiments, an *S. aureus* antibody is employed as the *S. aureus* reactant. "*S. aureus* antibody" refers to an immunoglobulin having the capacity to specifically bind a given antigen inclusive of antigen binding fragments thereof. The term "antibody" is intended to include whole antibodies of any isotype (IgG, IgA, IgM, IgE, etc), and fragments thereof which are also specifically reactive with a vertebrate (e.g. mammalian) protein. Antibodies can be fragmented using conventional techniques and the fragments screened for utility in the same manner as whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include F(ab'), F(ab)$_2$, Fv, and single chain antibodies (scFv) containing a VL and/or VH domain joined by a peptide linker. The scFv's can be covalently or non-covalently linked to form antibodies having two or more binding sites. Antibodies can be labeled with any detectable moieties known to one skilled in the art. In some aspects, the antibody that binds to an analyte one wishes to measure (the primary antibody) is not labeled, but is instead detected by binding of a labeled secondary antibody that specifically binds to the primary antibody.

Various *S. aureus* antibodies are known in the art. For example *S. aureus* antibodies are commercially available from Sigma and Accurate Chemical. Further, *S. aureus* antibodies are described in U.S. Pat. No. 4,902,616. The concentration of antibody employed is at least 2 nanograms/ml. Typically the concentration of antibody is at least 100 nanograms/ml. For example a concentration of 50 micrograms/ml can be employed. Typically no more than about 500 micrograms/ml are employed. As previously described, it is preferred to immobilize the *S. aureus* antibody on the surface of the acoustic mechanical biosensor.

In other embodiments, fibrinogen is employed as the *S. aureus* reactant. Without intending to be bound by theory, it is believed that a fibrinogen-binding protein expressed by the *S. aureus* bacteria reacts with the fibrinogen to produce a network of fibers called fibrin. This is a polymerization reaction commonly referred to as "clumping" that results in a physical change in viscosity and/or bound mass that can be detected by the SH-SAW biosensor.

The concentration of fibrinogen to produce this reaction is typically at least 0.0001 wt-% and generally no more than 5 wt-%. The reaction of fibrinogen and *S. aureus* can be used to change the viscosity of a liquid that can then in turn be detected by a SH-SAW biosensor for example. Alternatively, this fibrinogen reaction can be used to select and/or concentration *S. aureus* present as a sample preparation technique as previously described.

Human plasma and animal (e.g. rabbit) plasma are suitable fibrinogen-containing mediums. Commercially available plasma products generally include an anticoagulatant such as EDTA, citrate, heparin, etc. Fibrinogen derived from human is commercially available from Sigma Aldrich, St. Louis, Mo. under the trade designation "F4129".

It is generally preferred to employ relatively small volumes of test sample. Although test sample volume as high as 1-2 ml may be utilized, advantageously test samples on the order of 50 μl are generally sufficient. The ratio of test sample to fibrinogen-containing medium may vary. Typically, however, the ratio of fibrinogen-containing medium (e.g. solution) volume to test sample volume is on the order of magnitude of 10 to 1.

The rate of viscosity increase (e.g. rate of reaction of fibrinogen-binding protein expressed by the *S. aureus* bacteria with fibrinogen) is affected by various reaction conditions, some of which are described in the art. In order to obtain the shortest detection rates, it is preferred to optimize the reaction conditions.

In order to increase the rate of fibrinogen binding it is preferred to incorporated calcium ion into the test sample and/or fibrinogen containing medium. For ease in operation, it is typically preferred to incorporate calcium ion into the fibrinogen-containing solution. Typically, calcium ion is added in the form of hydrated salts such as $CaCl_2.2H_2O$. The concentration of calcium ion typically is at least 0.1 wt-% (e.g. 0.2, 0.3, 0.4) and more preferably at least 0.5 wt-%. The concentration of calcium ion is typically less than 2 wt-%. According to the literature zinc ion may have similar affect of the reaction rate.

Another factor that affects the reaction rate of fibrinogen binding is temperature. Preferably, the temperature at which the test sample and *S. aureus* are combined is less than 37° C. Further, the temperature is preferably greater than 5° C.

Although the acoustic mechanical biosensor may be operated at room temperature (i.e. 20-25° C.), fibrinogen binding is optimal at temperatures ranging from about 15° C. to about 25° C.

The present invention has now been described with reference to several specific embodiments foreseen by the inventor for which enabling descriptions are available. Insubstantial modifications of the invention, including modifications not presently foreseen, may nonetheless constitute equivalents thereto. Thus, the scope of the present invention should not be limited by the details and structures described herein, but rather solely by the following claims, and equivalents thereto.

SH-SAW Biosensors 1-3

Three different acoustic mechanical biosensors were used in the examples. All three biosensors employed leaky surface acoustic wave on YX $LiTaO_3$ at a rotation angle of about 36°.

Single-side polished 36° YX $LiTaO_3$ (Sawyer Research Products Inc., Eastlake, Ohio) wafers were initially cleaned by rinsing with acetone, methanol, isopropanol, and 18MΩ cm water, respectively, then dried with $N_2$. A lift-off procedure was used to define the interdigital transducers for each delay line. To promote adhesion, a 100 angstrom titanium (Ti) binding layer was evaporated on the $LiTaO_3$ wafers using an e-beam evaporator (CVC Products Inc.). An 800 angstrom gold layer was then deposited on the Ti film by resistive evaporation.

To protect the IDT patterns during dicing, AZ4110 photoresist was applied to the wafer and baked at 90° for 90 seconds. Prior to dicing, the fine ground side of the wafer was mounted on blue medium tack (Semiconductor Equipment Corp., Mesa, Ariz.). The wafers were then diced with a 1.8 mm width wheel, using a feed rate of 0.2 mm/s, and a spindle speed of 12,000 rpm.

A split double interdigital electrode configuration was patterned onto the $LiTaO_3$ wafers. This pattern was duplicated to create both active sensor and reference delay lines. The spacing between the delay lines was 130λ. The IDTs consisted of 56 finger pairs with an aperture of 38λ and a metallization ratio of n=0.5. The IDT center-to-center separation was 220λ. These devices supported SH waves with center frequencies at 103 MHz and an insertion loss of −8 dB.

SH-SAW biosensor 1 employed a waveguide having a 0.5 micron thick polyimide layer prepared by cleaning the sensor with N-methyl pyrolidone and exposure to high intensity UV light, spin coating a polyimide solution commercially available from HD Microsystems Ltd., Santa, Clara, Calif., under the trade designation "Polyimide 2613", and then curing the coating at 325° C. for about 4 hours. The polyimide was removed from the pads of the sensor such that only the delay lines were covered with the waveguide material.

SH-SAW biosensor 2 was prepared in the same manner as SH-SAW biosensor 1 except that polystyrene commercially available from Aldrich (catalog #18,242-7) in a 10% solids solution in toluene was spin coated to a thickness of 1.4 microns.

SH-SAW biosensor 3 included a tie layer disposed on the 0.5 micron thick polyimide waveguide, an immobilization layer disposed on the tie layer, and a S. aureus reactant (e.g. antibody) disposed on the immobilization layer. The layers were constructed as follow:

A parallel-plate capacitively coupled reactive ion etcher (obtained from Plasma Therm, St. Petersburg, Fla.) under the trade designation "Model 2480" was used to deposit a diamond like coating (DLC) using acetylene plasma onto a polyimide film and to deposit a diamond-like glass (DLG) coating using tetramethyl silane plasma onto the diamond like coating (DLC).

An approximately 20 cm by 30 cm sample of polyimide film (available under the trade designation "KAPTON E" from E.I. du Pont de Nemours & Co., Wilmington, Del.) was affixed to the powered electrode of the ion etcher using 3M 811 Adhesive Tape from 3M Company, St. Paul, Minn. The ion etcher chamber was closed and the chamber was pumped to a pressure of 0.67 Pa (0.005 Torr). Oxygen gas was introduced into the chamber at a flow rate of 500 standard $cm^3$ per minute, and the pressure of the chamber was maintained at 6.7 Pa (0.050 Torr). Plasma was ignited and was sustained at a power of 2000 W for 15 seconds. The oxygen gas flow was then terminated and the chamber was allowed to pump to a pressure of 0.67 Pa (0.005 Torr). Acetylene gas was then introduced into the chamber at a flow rate of 200 standard $cm^3$ per minute, and the pressure of the chamber was maintained at 2 Pa (0.015 Torr). Plasma was ignited and was sustained at a power of 1600 W for 10 seconds. The flow of acetylene gas was then terminated and the chamber was allowed to pump to a pressure of 0.67 Pa (0.005 Torr).

Oxygen gas was again introduced into the chamber at a flow rate of 500 standard $cm^3$ per minute and, the pressure of the chamber was maintained at 20 Pa (0.15 Torr). Plasma was ignited and was sustained at a power of 300 W for 10 seconds. With the oxygen gas flow rate maintained at 500 standard $cm^3$ per minute, tetramethylsilane gas was introduced into the chamber at a flow rate of 150 standard $cm^3$ per minute. The chamber pressure was maintained at 20 Pa (0.15 Torr). Plasma was ignited and was sustained at a power of 300 W for 12 seconds. The flow of tetramethylsilane gas was terminated. After a period of 1 minute, with both the flow of oxygen gas and the chamber pressure of 20 Pa (0.15 Torr) maintained, plasma was ignited and was sustained at a power of 300 W for 20 seconds. The flow of oxygen gas was then terminated and the chamber pressure was allowed to pump to a pressure of 0.67 Pa (0.005 Torr). The chamber was then opened to the atmosphere and the sample of polyimide film was removed from the powered electrode, turned so that the DLG coating faced the electrode, and was again affixed to the electrode. The sequence of plasma treatments was repeated to provide a sample of polyimide film with a DLC and a DLG coating on both sides.

The DLC/DLG coated sensor was immersed in a 5 ml N-acyl saccharin solution of 1 mM in dichloromethane for 15 mins. The sensor was removed and washed with more dichloromethane and dried in the lab nitrogen to form an immobilization layer.

The devices can be assembled as described in Applicants' Copending Applications, U.S. patent application Ser. No. 10/596,674 entitled "Estimating Propagation Velocity Through Surface Acoustic Wave Sensors", U.S. patent application Ser. No. 10/596,954 entitled "Surface Acoustic Wave Assemblies", and U.S. patent application Ser. No. 10/596,956 entitled "Acousto-mechanical Detection Systems and Methods for Biological Agents" filed the same date herewith.

Examples 1-7 illustrate the detection of S. aureus with an acoustic mechanical biosensor. Fibrinogen is employed as the S. aureus reactant. Examples 1-3 utilized SH-SAW Biosensor 1 having a polyimide waveguide, whereas Examples 4-6 utilized SH-SAW Biosensor 2, having a polystyrene waveguide. Example 7 utilized SH-SAW Biosensor 3. In each of Examples 1-7, the biosensor was placed in an incubator at 28° C. to prevent fluctuations and drift due to temperature difference.

EXAMPLE 1

S. aureus bacteria were obtained from The American Type Culture Collection, Rockville, Md. under the trade designation "ATCC 25923". The bacteria were grown in an 18 h broth culture (5 milliliters of Tryptic Soy Broth, Hardy Diagnostics, Santa Maria, Calif.) at 37C. The cultures were washed by centrifugation (8000 rpm/15 minutes) and resuspended in phosphate-buffered saline ("PBS buffer").

A 1% calcium ion solution was prepared from $CaCl_2 \cdot 2H_2O$.

A 0.5% solution of human fibrinogen (obtained from Sigma, Aldrich under the trade designation "F4129") was prepared by dilution in imidazole buffer of pH 7.35 (obtained from Sigma, Aldrich under the trade designation "I2900').

The biosensor was equilibrated in air to insure the biosensor had a magnitude of greater than −15 db and was stable. After equilibration in air, 329 µl of the 0.5% fibrinogen solution and 121 µl of the 1% calcium ion solution were combined, added to the biosensor pod, and allowed to equilibrate for 30 minutes. As a control, 50 µl of water was injected into the biosensor pod. The reaction was allowed to run for 30 minutes as recorded by the sensogram of FIG. 2. The "0" point on the x-axis is the point where water was injected. No change in phase or velocity was detected.

Figure 3A:
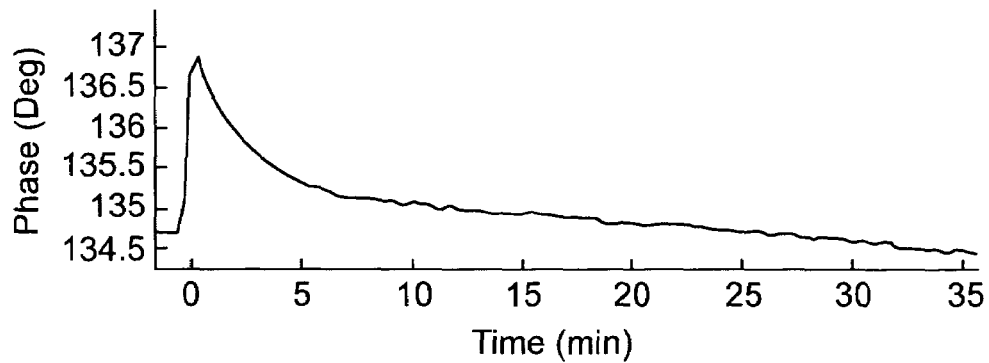

The biosensor pod was emptied and 450 µl of the fibrinogen and calcium mixture was added to the biosensor pod and allowed to equilibrate for 30 minutes. After which, 50 µl of the S. aureus bacteria solution having a concentration of 500 cfu/ml bacteria was added and the signal was monitored for 30 minutes. The resulting sensogram recorded by the biosensor is depicted in FIG. 3a.

EXAMPLE 2

Figure 3B:
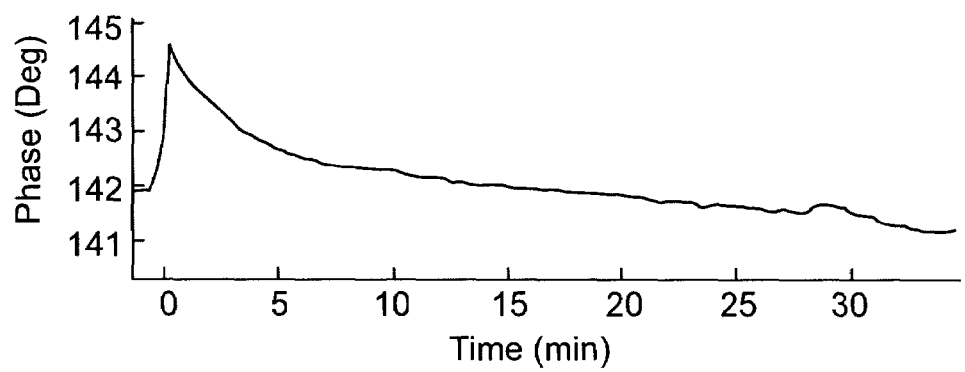

The procedure described in Example 1 was repeated with a S. aureus bacteria solution having a concentration of 5000 cfu/ml. The resulting sensogram recorded by the biosensor is depicted in FIG. 3b.

EXAMPLE 3

Figure 3C:
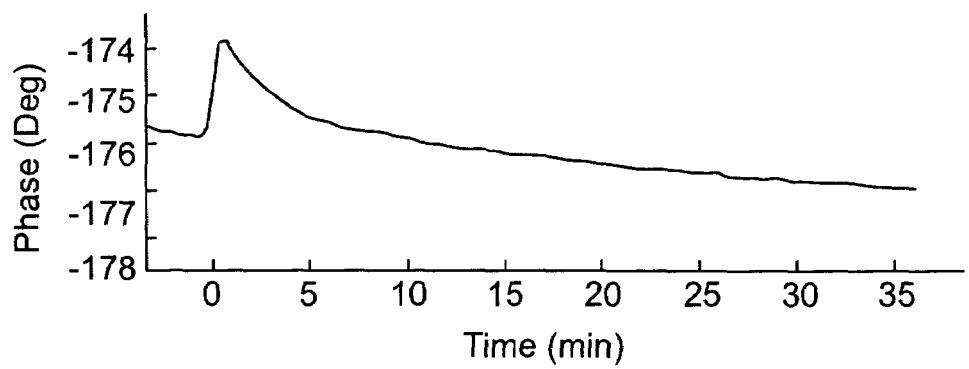

The procedure described in Example 1 was repeated with a S. aureus bacteria solution having a concentration of 50,000 cfu/ml. The resulting sensogram recorded by the biosensor is depicted in FIG. 3c.

EXAMPLE 4

Figure 4A:
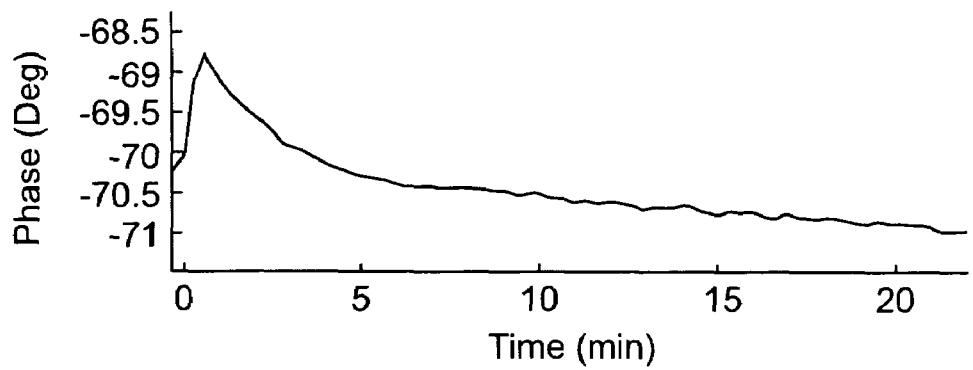

The procedure described in Example 1 was repeated (i.e. with a S. aureus bacteria solution having a concentration of 500 cfu/ml) with the exception that the polystyrene waveguide was utilized instead of the polyimide waveguide. The resulting sensogram recorded by the biosensor is depicted in FIG. 4a.

EXAMPLE 5

Figure 4B:
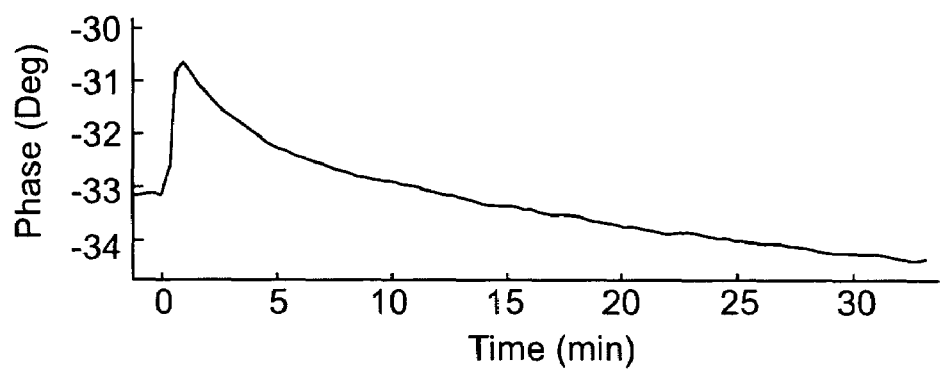

The procedure described in Example 2 was repeated (i.e. with a S. aureus bacteria solution having a concentration of 5000 cfu/ml) with the exception that the polystyrene waveguide was utilized instead of the polyimide waveguide. The resulting sensogram recorded by the biosensor is depicted in FIG. 4b.

EXAMPLE 6

Figure 4C:
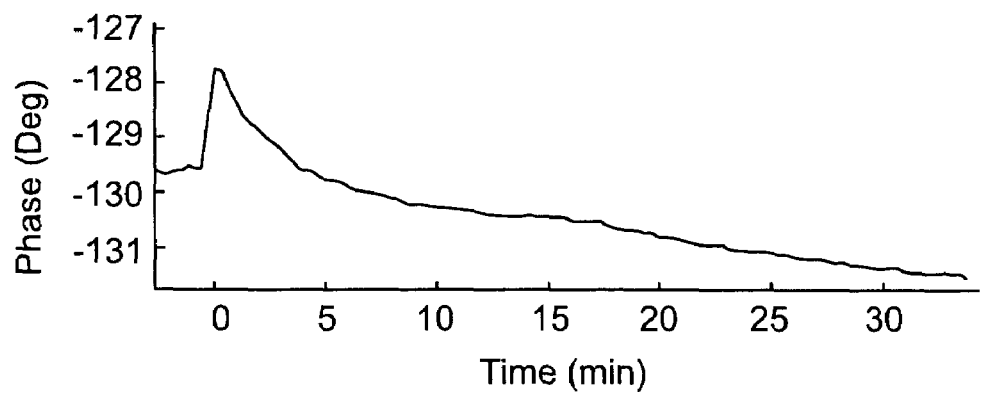

The procedure described in Example 3 was repeated (i.e. with a S. aureus bacteria solution having a concentration of 50,000 cfu/ml) with the exception that the polystyrene waveguide was utilized instead of the polyimide waveguide. The resulting sensogram recorded by the biosensor is depicted in FIG. 4c.

Figure 2:
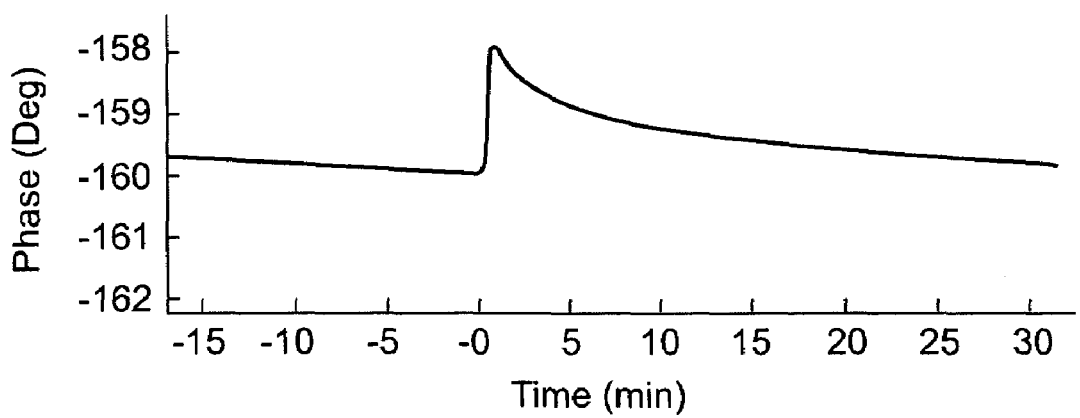
Figure 5:
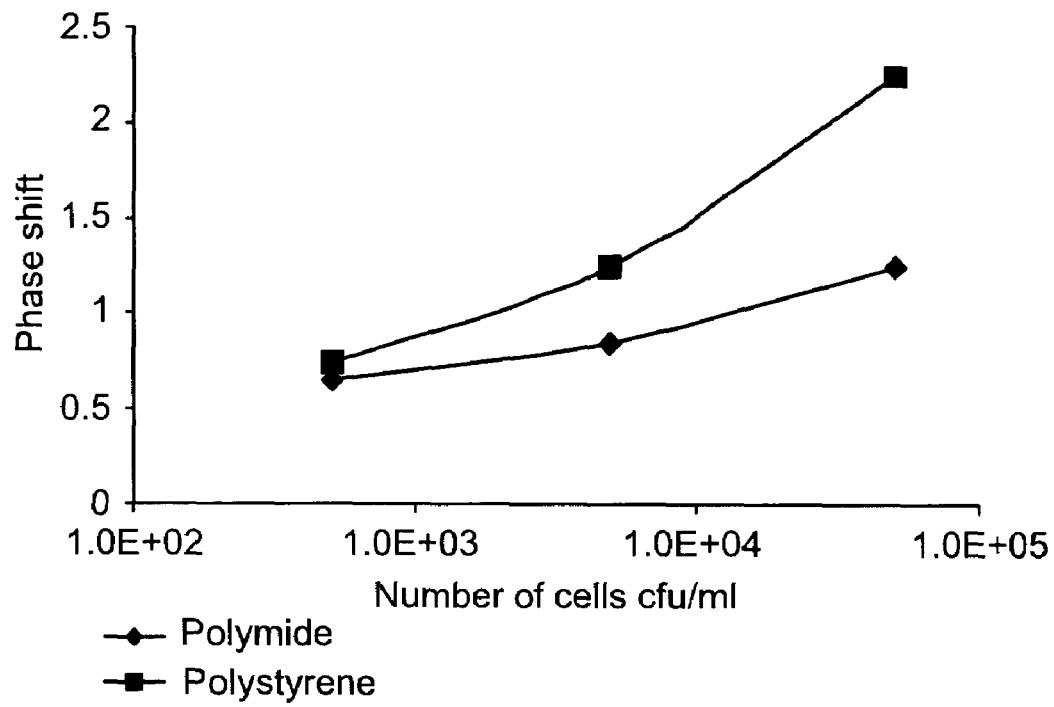

In comparison to FIG. 2, each of the sensograms of FIG. 3a-3c and FIG. 4a-4c depict a downward slope phase shift at each S. aureus bacteria injection. The magnitude of the phase shift was calculated by subtracting the phase value at the end of 30 minutes from the phase value at the start point (i.e. zero). The phase shift observed at the end of 30 minutes at various concentrations of S. aureus concentrations is depicted in FIG. 5.

Figure 6:
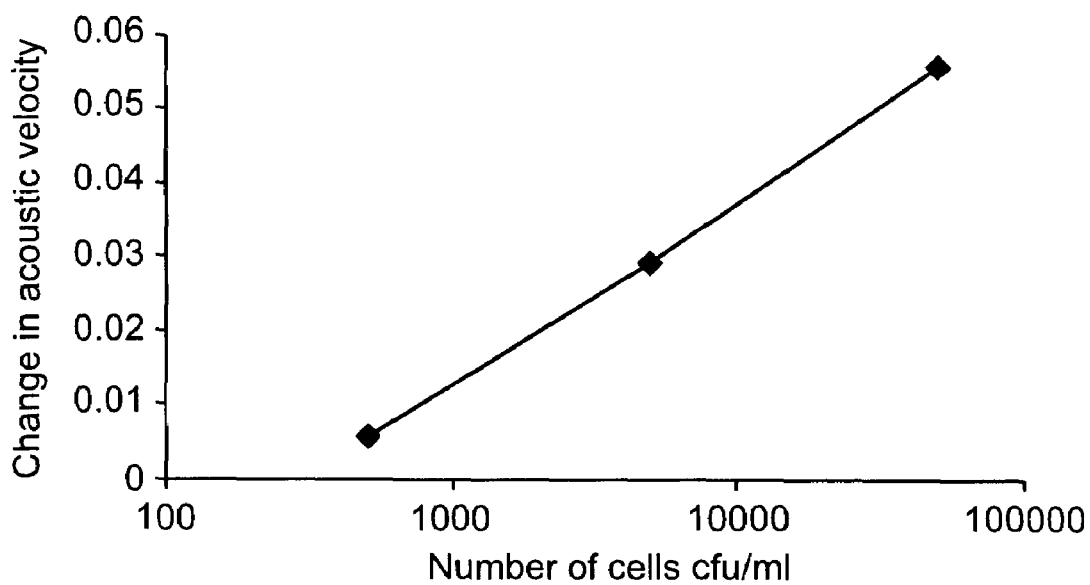

FIG. 6 shows the linear relationship between the change in propagation velocity as a function of S. aureus concentration utilizing the polyimide waveguide. The change in propagation velocity in calculated as described in Applicants' Copending U.S. patent application Ser. No. 10/596674 entitled "Estimating Propagation Velocity Through Surface Acoustic Wave Sensors", filed the same day herewith.

EXAMPLE 7

Example 7 is demonstrative of employing fibrinogen to bind to S. aureus bound at the biosensor surface thereby amplifying the detection signal.

A S. aureus reactant layer was prepared with rabbit S. aureus antibody (obtained from Accurate Chemical and Scientific Corporation, Westbury, N.Y. under the trade designation "Axell" number YVS6881, H6161) diluted to 50 µg/ml in 100 mM buffer salt solution (obtained from Sigma under the trade designation "CHES" at a pH of 9). A 15 µl aliquot of this solution was placed on the active side of the sensor. Similarly Chicken IgY antibody (obtained from Jackson Immunoresearch, West Grove, Pa. under the trade designation "Chrom-Pur Protein IgY") was diluted in the same manner and placed on the reference side. The antibodies were allowed to react with the immobilization layer for 30 minutes. The sensor was first washed in PBS buffer containing 0.1% (v/v) polyoxyethylene sorbitan monolaurate (obtained from Sigma under the trade designation "Tween 20") followed by being washed with only the PBS buffer. The sensor was stored in PBS buffer.

For SH-SAW biosensor 3, a six port valve was included in the flow set-up to which the syringe pump was connected passing buffer over the sensor and back into the waste. Another loop was attached to the six-port valve for bacteria injection. Yet another loop was connected to the six port valve for fibrinogen injection. A switch controlled the injection loop.

At the start of each experiment the sensor was placed in the sensor pod that was connected to the electronic board. A syringe pump was used to inject buffer at the rate of 5 ml/min, to flush any air bubbles. The rate was then set to 0.03 ml/min. The bacteria containing samples were loaded at the start of each experiment with the sample remaining in the loop until manual switching. The system was allowed to equilibrate with buffer flow until the $45^{th}$ data point, with 30 seconds for each data point. A sample containing S. aureas bacteria at a concentration of 1,000 cfu/ml was injected using the manual switch at this point. While this flow continued, the fibrinogen was loaded in one other loop in the six port valve and stayed there until further manual switching. Following the bacteria plug, the system was again allowed to equilibrate with the buffer at the rate of 0.03 ml/min for 70 data points before the fibrinogen was allowed to flow over the sensor by manual switching. The injection size varied depending on the volume of injection. The injection volume that flowed over the sensor was either 250 µl (time taken 8 min) or 350 µl (time taken 14 mins) or 500 µl (time taken 20 mins). The concentration of fibrinogen was varied between 0.1-0.5% and the injection loops changed like the bacteria loops. Phase and magnitude data was collected for the entire experiment and processed as mentioned below.

Phase shift was measured as the difference between the phase at the fibrinogen injection point and the phase at sample number (injection point +30 data points) for fibrinogen injections of 8 minutes. For the 20 minutes plugs phase shift was measured as the difference between the phase at injection point and the phase at sample number (injection +54 data points). It was found that phase shift alone exhibited statistically poor correlation to the S. Aureus concentration.

Upon examining the data of nineteen randomly chosen experiments consisting of 6 injections without bacteria and 13 injections with bacteria, it was discovered that there was a correlation between the phase shift and the drift in phase before injection of fibrinogen. In order to quantify this effect, a wavelet regression was used to model the entire phase response. The derivative of phase with respect to time was calculated at the injection time of fibrinogen and was used to quantify the drift before injection. Regression was then used to quantify the relationship between phase shift and the bacteria concentration as well as the phase derivative at the injection.

From the regression, it was found that the initial derivative in phase before injection has a statistically significant effect on the phase shift. The effect was significant enough that it was difficult to separate out the phase response caused by the fibrinogen injections from the overall phase response.

Based on this analysis, an algorithm was developed and used to define a modified phase shift that corrects for the initial drift before injection. The algorithm was implemented with software commercially available from Math Works under the trade designation "MATLAB". The algorithm consisted of:

filtering the data set to remove outliers;
calculating the sensor drift by modeling wave phase data response as a function of time using a suitable non-linear model;
  calculating the first derivative of the phase shift at a point wherein the fibrinogen is initially provided (i.e. the point of injection); and
  calculating an overall phase shift from the point wherein the fibrinogen is initially provided to a point wherein the totality of fibrinogen has passed over the sensing surface; and
calculating an estimated phase shift due to the sensor drift from a (e.g. linear) regression that quantifies the relationship between phase shift and sensor drift; and
calculating a modified phase shift by subtracting the estimated phase shift due to sensor drift form the overall phase shift.

Suitable non-linear models for modeling the phase response include wavelet regression, neural networks, multivariate adaptive, regression splines and the like.

The modified phase shift was calculated for all nineteen experiments. The modified phase shift of the samples without S. Aureus bacteria were compared to those experiment having 1,000 cfu/ml of S. Aureus bacteria.

From the analysis of variance it was determined that the 95% confidence interval for the difference between E0 (no bacteria) and E3 (bacteria at a concentration of 1,000 cfu/ml) was [−3.58, −0.92] with a mean of −2.25. In other words, a E3 injection produced a modified phase shift of 2.25 higher than what was obtained with a E0 injection and the difference is statistically significant. Thus an E3 injection of S. Aureus could be distinguished from a blank E0 injection using the modified phase shift.

The examples show that S. aureus can be detected at very low levels (e.g. 500 cfu/ml). The examples also show that S. aureus can be detected in relatively short durations of less than 30 minutes of time in comparison to classical tube and slide tests. The detection sensitivity and detection time can be amplified and improved for temperatures ranging from about 25° C. to about 15° C. The fibrinogen concentration may be increased to increase the reaction rate.

The complete disclosures of the patents, patent applications, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows

What is claimed is:

1. A method of detecting *Staphylococcus aureus* cells comprising
   providing a test sample suspected of comprising *Staphylococcus aureus*;
   providing a *Staphylococcus aureus* reactant;
   combining the test sample and the *Staphylococcus aureus* reactant wherein the test sample results in a change of at least one physical property detectable by a horizontal surface acoustical wave biosensor if *Staphylococcus aureus* is present; and
   detecting the change with the shear horizontal surface acoustical wave biosensor.

2. The method of claim 1 wherein the test sample comprises *Staphylococcus aureus* at a concentration of less than about $5 \times 10^4$ cfu/ml.

3. The method of claim 1 wherein the test sample comprises *Staphylococcus aureus* at a concentration of less than about $5 \times 10^3$ cfu/ml.

4. The method of claim 1 wherein the test sample comprises *Staphylococcus aureus* at a concentration of less than about 1000 cfu/ml.

5. The method of claim 1 wherein the test sample comprises *Staphylococcus aureus* at a concentration of about 500 cfu/ml.

6. The method of claim 1 wherein detecting the change occurs in less than 150 minutes.

7. The method of claim 1 wherein detecting the change occurs in less than 100 minutes.

8. The method of claim 1 wherein detecting the change occurs in less than 60 minutes.

9. The method of claim 1 wherein detecting the change occurs in about 30 minutes.

10. The method of claim 1 wherein the change in at least one physical property is a change in viscosity.

11. The method of claim 1 wherein the change in at least one physical property is a change in bound mass.

12. The method of claim 1 wherein detecting the change comprises a change in wave phase.

13. The method of claim 1 wherein detecting the change comprises a change in wave velocity.

14. The method of claim 1 wherein the test sample comprises a volume ranging from about 0.5 ml to about 1.5 ml.

15. The method of claim 1 wherein the step of combining the test sample with the *Staphylococcus aureus* reactant is conducted at a temperature in a range from about 5° C. to about 37° C.

16. The method of claim 1 wherein the step of combining the test sample with the *Staphylococcus aureus* reactant is conducted at a temperature in a range from about 15° C. to about 25° C.

17. The method of claim 1 wherein test sample further comprises calcium ion at a concentration ranging from about 0.1 wt-% to about 2 wt-%.

18. The method of claim 1 wherein the biosensor further comprises a polymeric waveguide.

19. The method of claim 18 wherein the waveguide is selected from polyimide and polystyrene.

20. The method of claim 1 wherein the *Staphylococcus aureus* reactant comprises of fibrinogen.

21. The method of claim 20 wherein the fibrinogen is present at a concentration ranging from 0.0001 wt-% to 5 wt-%.

22. The method of claim 1 wherein the *Staphylococcus aureus* reactant comprises plasma.

23. The method of claim 22 wherein the plasma is selected from human plasma and animal plasma.

24. The method of claim 1 wherein the *Staphylococcus aureus* reactant comprises fibrinogen solution.

25. The method of claim 1 wherein the *Staphylococcus aureus* reactant is provided in a liquid.

26. The method of claim 1 wherein the *Staphylococcus aureus* reactant is provided to the biosensor followed by providing the test sample to the biosensor.

27. The method of claim 1 wherein the test sample is provided to the biosensor followed by providing the *Staphylococcus aureus* reactant to the biosensor.

28. The method of claim 1 wherein the step of combining the test sample and *Staphylococcus aureus* reactant results in formation of a solid.

29. A method of detecting *Staphylococcus aureus* comprising providing a test sample suspected of comprising *Staphylococcus aureus;* providing fibrinogen;

combining the test sample and the fibrinogen wherein the test sample results in a change of at least one physical property detectable by an acoustical mechanical biosensor if *Staphylococcus aureus* is present; and detecting the change with an acoustical mechanical biosensor.

30. The method of claim 29 wherein the biosensor comprises a sensing surface comprising *Staphylococcus aureus* antibody reacted with an immobilization layer.

31. The method of claim 30 wherein the fibrinogen amplifies the detection of *Staphylococcus aureus* bound to the sensing surface.

32. The method of claim 31 wherein detecting the change comprises a wave phase shift.

33. The method of claim 32 wherein a modified wave phase shift is calculated by separating sensor drift from sensor response.

34. The method of claim 33 wherein the modified wave phase shift is calculated with an algorithm comprising filtering wave phase data to remove outliers;

calculating the sensor drift by modeling the wave phase data response as a function of time using a suitable non-linear model;

calculating a first derivative of the phase shift at a point wherein the fibrinogen is initially provided; and calculating an overall phase shift from the point wherein the fibrinogen is initially provided to a point wherein the totality of fibrinogen has passed over the sensing surface; and calculating an estimated phase shift due to the sensor drift from a regression that quantifies the relationship between phase shift and sensor drift; and calculating the modified phase shift by subtracting the estimated phase shift due to the sensor drift form the overall phase shift.

* * * * *

UNITED STATES PATENT AND TRADEMARK OFFICE
CERTIFICATE OF CORRECTION

PATENT NO. : 7,399,609 B2
APPLICATION NO. : 10/960491
DATED : July 15, 2008
INVENTOR(S) : Brinda B. Lakshmi It is certified that error appears in the above-identified patent and that said Letters Patent is hereby corrected as shown below:

On the Title Page, in Column 2, under (Other Publications)
Line 10, delete "Biomendical" and insert -- Biomedical --, therefor.
Line 45, after "action of" delete "a".

On Page 2, in Column 1, under (Other Publications)
Line 8, after "Bioelectronics;" delete ",".

On Page 2, in Column 2, under (Other Publications)
Line 1, delete "in" and insert -- In --, therefor.
Line 13, delete "Cowan;I" and insert -- Cowan I --, therefor.

Column 2
Line 58, delete "and or" and insert -- and/or --, therefor.

Column 3
Line 10, delete "FIG." and insert -- FIGS. --, therefor.
Line 14, delete "FIG." and insert -- FIGS. --, therefor.
Line 65, delete "60533177," and insert -- 60/533177, --, therefor.

Column 4
Line 51, delete "36°YXLiTaO$_3$" and insert -- 36° YXLiTaO$_3$ --, therefor.

Column 5
Line 2, delete "Albequerque," and insert -- Albuquerque, --, therefor.
Line 5, delete "36°YXLiTaO$_3$" and insert -- 36° YXLiTaO$_3$ --, therefor.
Line 25, delete "tricholoro" and insert -- trichloro --, therefor.
Line 38, delete "tricholoro" and insert -- trichloro --, therefor.

Column 7
Line 15, delete "liqu" and insert -- liquid or gas or more preferably a liquid. The test --, therefor.

Column 8
Line 35, delete "anticoagulatant" and insert -- anticoagulant --, therefor.
Line 55, delete "fibrinogen containing" and insert -- fibrinogen-containing --, therefor.
Line 58, delete "CaCl$_2$.2H$_2$O" and insert -- CaCl$_2$·2H$_2$O --, therefor.

Column 9
Line 46, delete "pyrolidone" and insert -- pyrrolidone --, therefor.

UNITED STATES PATENT AND TRADEMARK OFFICE
CERTIFICATE OF CORRECTION

PATENT NO. : 7,399,609 B2
APPLICATION NO. : 10/960491
DATED : July 15, 2008
INVENTOR(S) : Brinda B. Lakshmi It is certified that error appears in the above-identified patent and that said Letters Patent is hereby corrected as shown below:

<u>Column 11</u>
Line 12, delete "$CaCl_2.2H_2O$." and insert -- $CaCl_2·2H_2O$. --, therefor.
Line 16, delete ""I2900')." and insert -- "I2900"). --, therefor.

<u>Column 12</u>
Line 62, delete "aureas" and insert -- aureus --, therefor.

<u>Column 14</u>
Line 27, after "follows" insert -- : --.

Signed and Sealed this

Twenty-third Day of September, 2008

JON W. DUDAS
*Director of the United States Patent and Trademark Office*